United States Patent [19]

Ogino et al.

[11] Patent Number: 5,005,492
[45] Date of Patent: Apr. 9, 1991

[54] TABLE MECHANISM

[75] Inventors: Sumihito Ogino; Ryo Takahashi, both of Tokyo, Japan

[73] Assignee: Yokogawa Medical Systems, Limited, Tokyo, Japan

[21] Appl. No.: 587,628

[22] Filed: Sep. 24, 1990

Related U.S. Application Data

[63] Continuation of Ser. No. 432,766, filed as PCT JP88/00412 on Apr. 27, 1988, published as WO88/08494 on Nov. 3, 1988, abandoned.

[30] Foreign Application Priority Data

Apr. 28, 1987 [JP] Japan .............................. 62-64373[U]

[51] Int. Cl.$^5$ ................................................ A47B 9/00
[52] U.S. Cl. ....................................... 108/145; 297/346
[58] Field of Search ........................ 108/144, 145, 148; 297/346

[56] References Cited

U.S. PATENT DOCUMENTS 2,490,341 12/1949 Davis et al. .......................... 297/346

FOREIGN PATENT DOCUMENTS 1053331 3/1959 Fed. Rep. of Germany ...... 108/145
47-16932 5/1972 Japan .
60-139963 7/1985 Japan .

Primary Examiner—Kenneth J. Dorner
Assistant Examiner—Gerald A. Anderson
Attorney, Agent, or Firm—Moonray Kojima

[57] ABSTRACT

A table mechanism for lifting and lowering a table top through a parallel link mechanism. In the table mechanism of the invention, which does not cause an increase in costs even when an initial position of the table top is set low in spite of having a cover for coversing side surfaces of a parallel link mechanism, there is given a difference of elevation in the fitting position of the parallel link mechanism on the sides of the table top and of the floor in combination with front and rear links.

1 Claim, 3 Drawing Sheets

TABLE MECHANISM

This is a continuation of application Ser. No. 07/432,766, filed as PCT JP88/00412 on Apr. 27, 1988, published as WO88/08494 on Nov. 1988, now abandoned.

BACKGROUND OF THE INVENTION

1. Field of the Invention

The present invention relates to an improvement of a table mechanism for lifting and lowering a table top by use of a parallel link mechanism.

2. Description of the Prior Art

Turning to FIG. 4, there is illustrated a typical example of a conventional table mechanism for lifting and lowering a table top through a parallel link mechanism. FIG. 4 is a view showing a concept of the table mechanism for use with a computerized tomograph. Referring again to FIG. 4, a table mechanism 1 is arranged such that a table top 2 is supported on a link mechanism 5 composed of two parallel links 3 and 4 parallel with each other. The table mechanism 1 is so installed as to be substantially orthogonal to a front face of a gantry 6 in the longitudinal direction. One ends of the two links 3 and 4 are rotatably fitted to a base 7, while the other ends thereof are rotatably fitted to a table top supporting unit 8. The link mechanism 5 driven by a driving mechanism 9, with its inclination being varied, behaves to lift and lower the table top while being held in parallel with a base 7. Solid lines and one-dotted lines respectively indicate two kinds of states of the table top 2, the link mechanism 5 and the driving mechanism 9, which are developed as a result of such moving operations. More specifically, the solid lines indicate a state of the table mechanism 1 (hereinafter referred to as an imaging position) when inserting a cradle 10 into an gantry opening 11, while the one-dotted lines show a state of the table mechanism (hereinafter referred to as an initial position) when mounting a subject for examination. The table top 2 is situated lowest in the initial position, which is preferably as low as possible to facilitate mounting of the subject. Side surfaces of the link mechanism are covered with an adequate cover in terms of security and appearance. FIG. 5 is a block diagram depicting a conventional example of a cover for covering the side surfaces of the link mechanism. The cover is composed of a plurality of cover pieces 12 and fitting plates 13 and 14, provided on the table top and on the base, for rotatably securing both ends of the cover pieces. Each of the cover pieces 12 assumes a substantially rectangular shape having a nearly equal length to that of the link 3 or 4. Spacings at which the cover pieces 12 are secured are set taking widths thereof into consideration. Namely, the spacings are set so that the cover pieces adjacent to each other cover the side surfaces of the parallel link mechanism 5 with no gap while being invariably overlapped with each other. As a result, the side surfaces of the parallel link mechanism 5 are covered with the cover pieces 12 in the imaging position or in the initial position. Turning to FIG. 6, there is schematically illustrated an array of the cover pieces 12. To be specific, the rectangular cover piece 12 having a width W is secured in such a manner that a stopping part 12a conceived as a corner of the rectangle is spaced a distance L away from a base surface 15. The distance L is so set that a corner 12c of the cover piece 12 does not touch the base surface 15. As is obvious from the Figure, if the initial position is made lower than before at the thus set distance L, it is required that the cover piece width W be smaller than in the previous case. If the cover piece width W is diminished, a greater number of cover pieces are needed for covering the side surfaces of the link mechanism. Consequently, there arises a problem of being costly due to an increase in the number of cover pieces when actualizing a device incorporating a link mechanism providing a lower initial position.

SUMMARY OF THE INVENTION

It is a primary object of the present invention to provide a table mechanism equipped with a cover for covering side surfaces of a link mechanism, which is capable of restraining an increase in costs even when an initial position of a table top is set low.

To accomplish this object, according to one aspect of the invention, there is provided a table mechanism for lifting and lowering a table top through a parallel link mechanism, characterized in that a mounting position of the link mechanism on the sides of the table top and the floor is given a difference of elevation in a vertical direction in combination with front and rear links.

BRIEF DESCRIPTION OF THE DRAWINGS

Other objects and advantages of the invention will become apparent during the following discussion taken in conjunction with the accompanying drawings, in which.

DESCRIPTION OF THE PREFERRED EMBODIMENT

The present invention will hereinafter be described in detail with reference to the accompanying drawings.

Figure 1:
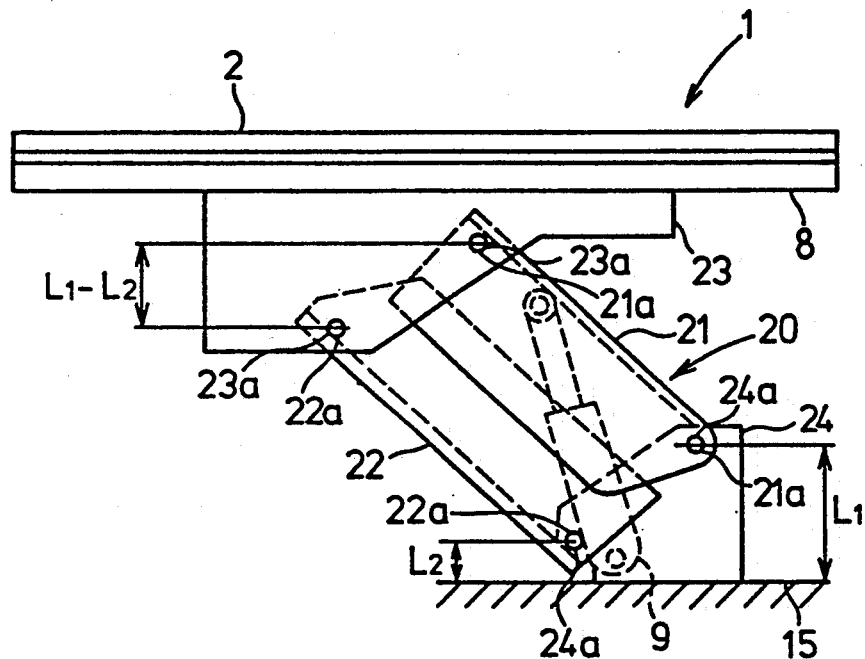
FIG. 1 is a block diagram depicting a principal portion of a table mechanism in one embodiment of the present invention
Figure 2:
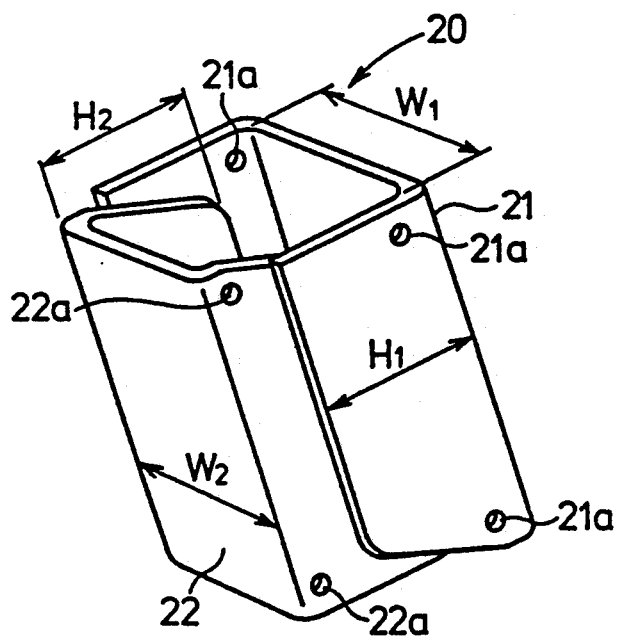
FIG. 2 is a block diagram illustrating a link mechanism in one embodiment of the invention.
Figure 4:
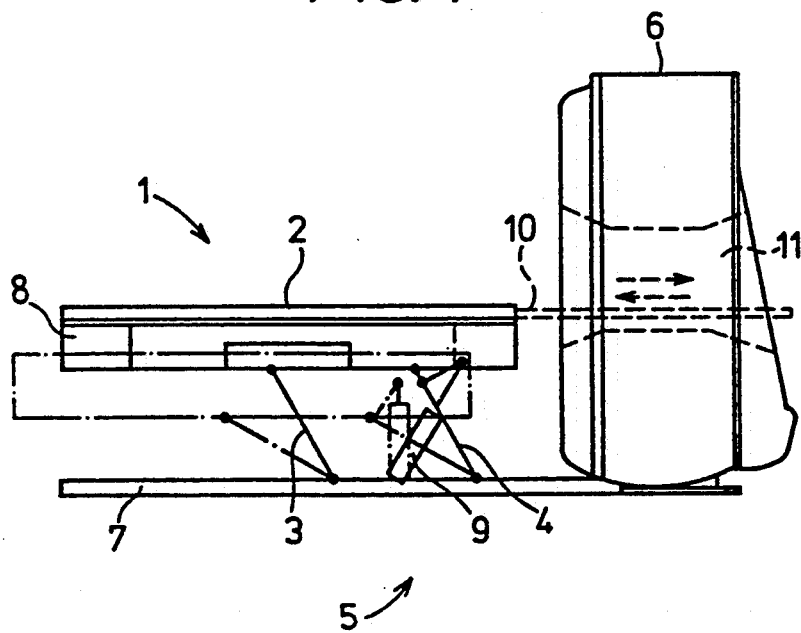
FIG. 4 is a block diagram showing a prior art example.
Figure 5:
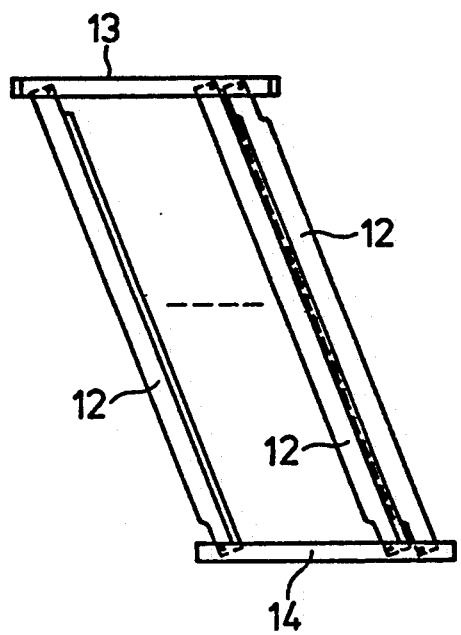
FIG. 5 is a block diagram illustrating cover pieces in the prior art example.
Figure 6:
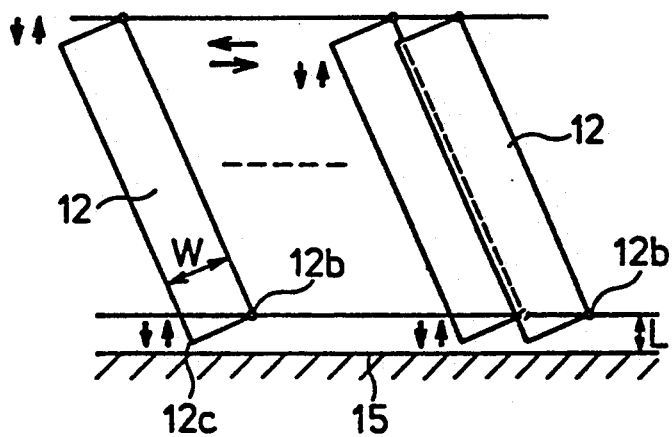
FIG. 6 is a schematic diagram depicting states of the cover pieces in association with a movement of the table top.

Referring first to FIGS. 1 and 2, there are shown block diagrams of one embodiment of the invention. FIG. 1 depicts a principal portion of a table mechanism. FIG. 2 is shows a link mechanism in perspective. In these Figures, the components marked with the same symbols in FIG. 4 have the like functions. A link mechanism 20 consists of a front link 20 and a rear link 22, both ends of which are rotatably attached to a table top side base 23 and a floor side base 24. These two bases are respectively provided with rotary shafts 23a and 24a, inserted into holes 21a and 22a formed in both ends of the links, for rotatably supporting these links. On the underside, though not illustrated, there are likewise provided four holes and rotary shafts corresponding thereto. The front link 21 and the rear link 22 fitted to the table top side base 23 and the floor side base 24 cooperate to constitute a parallelogrammic link. In the floor side base 24, a fitting shaft 24a for the front link 21 is disposed in a position having a height L1 from the floor face, while a fitting shaft 24a for the rear link 22 is disposed in a position having a height L2 therefrom, wherein L1>L2. In the table top side base 23, fitting shafts 23a for the front and rear links 21 and 22 are installed with a difference of elevation therebeween which is given by L1-L2. In spite of the difference of elevation between the fitting parts for the front and rear links 21 and 22, the table top side base 23 and the floor side base 24 are so shaped that their upper and bottom surfaces are parallel with the floor face. One end of the driving mechanism 9 is rotatably secured to the floor side base 24, while the other end is rotatably secured to the front link 21. An inclination of the link mechanism varies due to expansion and contraction of the driving mechanism, and the table top 2 is lifted and lowered keeping the parallelism with the floor face.

FIG. 2 shows a detailed correlation between the front link 21 and the rear link 22. That is, the front link 21 is composed of a tub-like rigid member having an inner width W1, and the rear link is composed of a tub-like rigid member having an outer width W2 (<W1). A side wall assuming a tub-like shape is hereinafter referred to as a cover. A part of the cover unit of the rear link 22 is set inwardly of the cover unit of the front link 21, thus forming overlaps of the cover units of two links. Widths H1 and H2 of the respective cover units are set so that the overlaps are always formed in any inclined state ranging from the initial position to the imaging position. Note that the cover unit fundamentally assumes a rectangle. In an actual device, however, the rectangular configuration is partly cut off in the light of function of the link mechanism and ornamental effects as well.

Figure 3A:
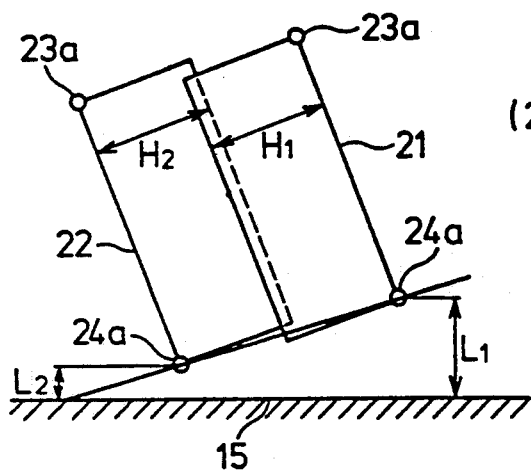
FIGS. 3A and 3B are schematic diagrams each showing the link mechanism in an imaging position and in an initial position in one embodiment of the invention.
Figure 3B:
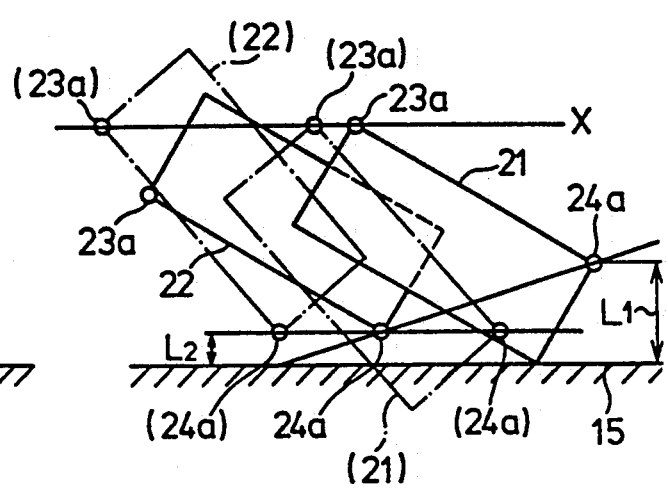

Based on this construction, there will be given schematic representations of states of the link mechanism 20 in association with the table top 2's movement from the imaging position to the initial position. FIG. 3A depicts a state in the imaging position. FIG. 3B depicts a state in the initial position. Referring to FIGS. 3A and 3B, the individual cover units of the front and rear links 21 and 22 are formed in the rectangular shape, and the rotary shafts thereof are positioned at the corners of the rectangles. In any state, there are provided the overlaps of the cover units of the front and rear links 21 and 22. Hence, the cover units perform functions similar to those of the cover pieces of the conventional cover. It is to be noted that a link mechanism drawn with the one-dotted lines in FIG. 3B is exemplified for a comparison with a case of giving no difference of elevation between the rotary shafts of the front and rear links 21 and 22. In this case, an inclination of the link mechanism is set large, and the table top is lowered down to the initial position, at which time a corner of the cover unit of the front link (21) comes in contact with a floor face 15 before a rotary shaft (23a) reaches a height X of the initial position. Thus, a further descent can be prevented. Therefore, a width of the cover unit of the front link (21) has to be small to lower the rotary shaft (23a) down to an initial line X. In contrast, according to the construction of the invention, it is possible to set the initial position at a low level, while the cover units of the front and rear links 21 and 22 have large widths. Referring again to FIG. 3B, a parallelogram defined by four rotary shafts associated with the links according to the invention which are indicated by solid lines exhibits a smaller amount of collapse when the table top is situated in the lowest position than in a quadrangle defined by four rotary shafts relative to the links depicted with one-dotted lines for a comparison. Hence, the driving mechanism 9 bears less burdens on the basis of the construction of the present invention than in the prior art.

Note that the present invention is not limited to the above-described embodiment, and the table mechanism thereof is usable for an NMR imaging device. The link mechanism is not necessarily constituted by the tub-like member but may be constructed by combining rod-like parallel links with a cover.

Although the preferred embodiment for putting the invention into a practical use has been described, a variety modifications can be effected by one skilled in the art to which the invention belongs without departing from the scope of the following claims.

What is claimed is:

1. A table top lifting mechanism comprising
   a pair of links disposed parallel to each other and each having a first end and a second end;
   first fitting means for rotatably fitting said pair of links by said first end of each of said pair of links to said table top with one of said pair of links being disposed at a higher vertical position than the other of said pair of links with a predetermined vertical distance therebetween;
   second fitting means for rotatably fitting said pair of links by said second end of each of said pair of links to a base structure with one of said pair of links being disposed at a higher vertical position than the other of said pair of links with the same predetermined vertical distance therebetween; and
   driving means having one end thereof rotatably secured to one of said pair of links, and another end thereof secured to said base structure;
   wherein each of said pair of links comprises a U-shaped member in section with the longitudinal dimension extending the length of said links;
   wherein the open ended part of one U-shaped member is fitted longitudinally over the open ended part of the other U-shaped member along the length of said links so as to overlap along the length during the entire time there is movement of the links during lifting operation; and
   wherein said driving means is concealed by said U-shaped members.

* * * * *